(12) United States Patent
Freiburger

(10) Patent No.: US 6,176,830 B1
(45) Date of Patent: Jan. 23, 2001

(54) METHOD AND SYSTEM FOR PRE-DETERMINING SPECTRAL DOPPLER USER PARAMETERS

(75) Inventor: Paul D. Freiburger, Bellevue, WA (US)

(73) Assignee: Siemens Medical Systems, Inc., Iselin, NJ (US)

( * ) Notice: Under 35 U.S.C. 154(b), the term of this patent shall be extended for 0 days.

(21) Appl. No.: 09/361,679

(22) Filed: Jul. 27, 1999

(51) Int. Cl.[7] .................................................... A61B 8/00
(52) U.S. Cl. ............................................................ 600/453
(58) Field of Search .................................... 600/455, 447, 600/454, 456, 443; 128/916

(56) References Cited

U.S. PATENT DOCUMENTS

| | | | |
|---|---|---|---|
| 5,443,071 | 8/1995 | Banjanin et al. | 128/661.09 |
| 5,487,389 | * 1/1996 | Banjanin et al. | 600/455 |
| 5,513,640 | * 5/1996 | Yamazaki et al. | 600/455 |
| 5,522,393 | * 6/1996 | Phillips et al. | 600/455 |
| 5,555,534 | 9/1996 | Maslak et al. | 367/135 |
| 5,682,896 | 11/1997 | Scheib et al. | 128/661.1 |
| 5,782,766 | 7/1998 | Weng et al. | 600/443 |

* cited by examiner

Primary Examiner—Marvin M. Lateef
Assistant Examiner—Maulin Patel

(57) ABSTRACT

A method of initializing a spectral Doppler mode of operation for an ultrasonic system includes acquiring ultrasound-based data during a two-dimensional mode of operation for a particular examination session and includes automatically establishing settings for the Doppler mode operation parameters based upon the ultrasound-based data. That is, the ultrasound-based data is processed during the session to select spectral Doppler mode settings that are specific to the ongoing session. The session-specific settings are invoked when the system is switched to the spectral Doppler mode. If the two-dimensional mode is a colorflow mode, the Doppler sample volume can be based upon detecting the location of maximum velocity in the colorflow image, the angle correct setting can be based upon maximum velocities in colorflow vectors, the pulse repetition frequency setting can be based upon the maximum frequency shift detected in the colorflow data, and the gain setting can be based upon the amplitude of colorflow data. On the other hand, if the two-dimensional mode is a power mode, the Doppler sample volume is based upon detecting the region of the power mode image having the strongest signals, the angle correct setting can be based upon detecting the direction of flow, the Doppler pulse repetition frequency can be based upon a scale setting for the power mode data acquisition, and a gain setting can be based upon the amplitude of power mode data. Lastly, if the two-dimensional mode is the grey-scale imaging mode, the selection of a Doppler sample volume can be based upon identifying a dark region near the center of the grey-scale image, the angle correct setting can be based upon the orientation of the boundaries of the identified dark region, and the gain setting can be based upon the amplitude of image data.

19 Claims, 4 Drawing Sheets

METHOD AND SYSTEM FOR PRE-DETERMINING SPECTRAL DOPPLER USER PARAMETERS

TECHNICAL FIELD

The invention relates generally to a method and a system for selecting settings for process parameters in an ultrasonic examination and relates more particularly to selecting settings for process parameters upon switching an ultrasonic system from a two-dimensional mode of operation to a spectral Doppler mode of operation.

DESCRIPTION OF THE RELATED ART

Ultrasonic imaging techniques may be used to produce images of internal features of an object, such as tissues of a human body. A diagnostic ultrasonic imaging system for medical use forms images of internal tissues of the human body by electrically exciting an acoustic transducer element or an array of acoustic transducer elements to generate ultrasonic beams that propagate into the patient's body. Energy of the ultrasonic beams reflects off human tissues that present discontinuities or impedance changes to the propagating ultrasonic beams. The echoes from the tissues are sensed by the transducer and are converted into electrical signals that are amplified and decoded to provide interrogation information. Ultrasonic imaging provides physicians with the real-time images of the internal features of the human anatomy without resorting to more invasive exploratory techniques, such as surgery.

An ultrasonic system has a number of modes of operation. One set of modes can be referred to collectively as "two-dimensional modes." Typically, frames of information are generated when the system is in one of the two-dimensional modes. Electrical signals are collected from the array of transducer elements to form each frame. The frame is a multi-pixel array in which each pixel corresponds to a location in a two-dimensional slice of the imaged tissue. Optionally, two-dimensional slices can be accumulated to form a three-dimensional ultrasonic image.

As an alternative to the two-dimensional modes of operation, an ultrasonic system can be operated in a spectral Doppler mode. In this mode, the interrogation takes place for a single target, such as a particular blood vessel. When the system is in the spectral Doppler mode, information may be processed to identify the velocity spectrum of the target over time. The results of the spectral Doppler mode of operation are conventionally presented by means of an audio signal that is responsive to a frequency spectrum, but visual displays are also used (e.g., the plotting of the velocity spectrum against time).

Returning to the set of two-dimensional modes of operation of the ultrasonic system, one such mode provides B-mode imaging. Echoes from a selected cross section are processed to form an image that is based on echo signal intensity. Conventionally, a grey-scale image provides a two-dimensional display of the cross section. Data returned from each transmission of a beam into the body of interest is used to determine a pixel value for the grey-scale image.

A second two-dimensional mode is referred to as colorflow imaging or BC imaging. In this mode, a color-coded velocity map is generated. At each pixel in the display, color is a function of the velocity of a corresponding physical region within a sample volume. Doppler shifts caused by blood flow are detected and used to determine the color of pixels. The color coding of pixels is often incorporated into grey-scale image information. Motion toward the acoustic transducer array may be represented by the color red, while motion away from the transducer array may be represented by the color blue. Unlike B mode operation, each pixel value of motion data is acquired by identifying differences in tissue positions over an "ensemble" of transmit-receive cycles. Thus, a time series of pixel values is compared to detect the changes in tissue location during the time series.

A third type of two-dimensional imaging is referred to as power mode imaging or BP mode imaging. This mode is similar to BC mode operation with respect to utilizing an ensemble of data frames to determine motion data, but the BP imaging is speed based, rather than velocity based. That is, the BP mode is direction independent. When an ultrasonic system is in the BP mode of operation, the displayed color for each pixel is a function of the speed of movement in the corresponding physical region of a sample volume. Red may be the selected color, with the intensity at each pixel being based upon the speed of motion within the physical region corresponding to the pixel.

Often, the spectral Doppler mode of operation follows two-dimensional imaging in order to provide information that is not available from the two-dimensional imaging. One of the limitations of colorflow imaging is described in U.S. Pat. No. 5,443,071 to Banjanin et al., which is assigned to the assignee of the present invention. Colorflow imaging measures blood flow velocity in a blood vessel by using a Doppler frequency shift which is obtained by analyzing the echoes received from the region of interest. However, the measure of blood flow velocity is a function of the angle of blood flow with respect to the direction of the interrogation beam. Thus, without information regarding the blood flow angle, the measured blood flow velocity is only an indication of the velocity in the direction of the interrogation beam. In order to overcome this deficiency, the operator (e.g., clinician) manually adjusts a Doppler "angle correct" setting. If a transducer array is not perpendicular to the vascular volume flow, an angle correct compensation may be used to provide a more accurate velocity measurement. The clinician may manually move the transducer array, may steer the interrogation beam from a stationary transducer array, or may provide angle correct compensation in computer processing (using the angle correct setting). As noted in the Banjanin et al. patent, the manual angle correction of blood flow velocity is often cumbersome and hard to repeat.

In addition to the error correct setting, there are settings of other operation parameters that are specific to the spectral Doppler mode of operation. For example, a Doppler pulse repetition frequency (PRF) must be set. The PRF setting determines the number of pulses that are transmitted per unit of time. The Doppler PRF is set to minimize the likelihood of interference when the beam is minimized. Another setting of concern is Doppler gain. The Doppler gain is the amplification of signals received from the transducer array. The gain is set higher if the signal strength is low. As another concern, the sample volume placement for the spectral Doppler mode is typically different than that of the two-dimensional mode. The spectral Doppler sample volume has a particular target which is much narrower than the sample volume of the preceding two-dimensional mode of operation.

Since there are a number of operation parameters that must be set when the spectral Doppler mode is initiated, the examination process is often time consuming. The clinician is required to determine the settings. It is not uncommon for the target of interest to move while the clinician is setting up the Doppler parameters (e.g., as a result of breathing). This causes the clinician to have to cycle through several modeto-mode iterations. The process can be expedited by establishing default settings for the Doppler operation parameters. For example, the gain setting may be automatically set to unity. The default settings may be estimations based upon an "average" examination. The clinician can then fine tune the settings for the specific examination. While this basis for establishing initial settings reduces the time required for an examination, there are a large number of variables that play a role in determining the settings, so that very few examinations match the typical examination.

What is needed is a method and an ultrasonic system for reducing the complexity of the procedure of switching from one of the two-dimensional modes of operation to a spectral Doppler mode of operation, thereby reducing the time and potentially improving the results of Doppler examinations.

SUMMARY OF THE INVENTION

A method of initializing a spectral Doppler mode of operation for an ultrasonic system includes acquiring ultrasound-based data during a two-dimensional mode of operation for a particular examination session and includes automatically establishing settings for Doppler mode operation parameters based upon the ultrasound-based data. Automated techniques are utilized to process the ultrasound-based data of the session in order to select settings that are to be implemented when the system is switched to the spectral Doppler mode. Thus, initial settings for the operation parameters that are specific to the spectral Doppler mode are based upon the particular session, rather than "average" session that determines default settings.

In one embodiment, the colorflow mode (BC mode) is the two-dimensional mode in which the ultrasound-based data is acquired and processed to select the settings. Preferably, the setting-related processing occurs in parallel with the conventional processing for generating a colorflow map of velocity. Consequently, the settings can be initiated quickly after the ultrasonic system is switched to the spectral Doppler mode (D mode). The parallel processing does not reduce the time required for the colorflow mapping.

The target of interest during the spectral Doppler mode of operation may be determined at least partially based upon the maximum velocity detected in the colorflow imaging. The Doppler sample volume could initially be centered at the location of the maximum velocity in the colorflow image. This would be more accurate and more easily repeated than the current method of requiring a clinician to visually determine the location of the maximum velocity on a colorflow image. A more robust selection can be provided by calculating the maximum velocity over several colorflow images and over several pixels.

An initial setting for the Doppler angle correct setting can be selected based upon the direction of flow in the colorflow image. The flow direction can be calculated in a number of alternative ways. For example, a line can be fit between the locations of maximum velocities in multiple colorflow vectors around the BC sample volume. Another possibility is to fit a line among the locations of peak cross-correlation coefficients calculated on the colorflow vectors around the BC sample volume location. These calculations specify the initial angle correct setting based on the direction of flow, since "angle correct" is intended to offset the impreciseness in the velocity flow measurement as a result of interrogating at a non-perpendicular angle. A less desirable method for determining the error correct setting would be to set the setting parallel to the boundaries of the colorflow signal in the vectors around the location of the sample volume.

The pulse repetition frequency (PRF) setting may be selected by detecting the maximum velocity in the colorflow image. The Doppler PRF should be set so that the frequency range above or below the baseline (depending on the type of examination) is greater than the maximum frequency shift detected in the colorflow data. A margin of a few percent may also be incorporated into this setting in order to avoid aliasing.

With regard to the gain in the spectral Doppler mode, the amplitude of the colorflow data around the sample volume can be used to provide an initial setting. The D mode signal strength is likely to be proportional to the colorflow signal strength.

In a second embodiment, the power mode (BP mode) is the condition of operation for the ultrasonic system during which the ultrasound-based data is acquired and processed to select initial settings for D mode operation. Again, the setting-related processing occurs in parallel with the conventional processing for generating a two-dimensional display. A BP image does not provide all of the information that is necessary for a BC image, since the BP image is direction independent. However, settings for the D mode parameters may be estimated from the BP image information that is acquired. Within a BP image, the strongest signals are typically produced in the region with the highest flow velocity. The region of the power mode image with the highest amplitude may be assumed to be the region of interest for spectral Doppler operation. Use of this assumption is not ideal, but the automated method provides an improvement over the currently used manual method. At the least, the power mode data can be used to locate the initial Doppler sample volume inside a particular blood vessel.

The direction of flow could be estimated in one of the manners described with reference to the embodiment in which BC imaging precedes the D mode operation. The significant difference would be that power mode data would be used instead of colorflow data. The maximum velocity information would not be present in a BP image, but the scale setting for the power mode acquisition could be used as a reasonably reliable starting point. If the scale setting was used in place of the actual maximum velocity shift, the Doppler PRF could be determined as described with reference to the BC mode embodiment. With regard to the D mode gain setting, the amplitude of the power mode data could be used in the same manner described with reference to the BC mode embodiment.

In a third embodiment, the initial mode is the B mode for operation of the ultrasonic system. In this B mode, only a few settings for operation parameters for the D mode can be estimated. The blood vessel of interest will most likely be located near the center of the image. The system could search for a dark region within the grey-scale image. If the dark region is near the center of the grey-scale image, the D mode sample volume may be set to coincide with the dark region. With regard to the angle correct setting, once a dark region has been located, a search can be performed for the orientation of the boundaries of that dark region. The angle correct could be set parallel to the boundaries. While the method and system have been described as being used with two-dimensional imaging, it should be understood that the method and system apply equally to three-dimensional systems. Typically, a three-dimensional image is formed by combining slices of two-dimensional images.

DETAILED DESCRIPTION

Figure 1:
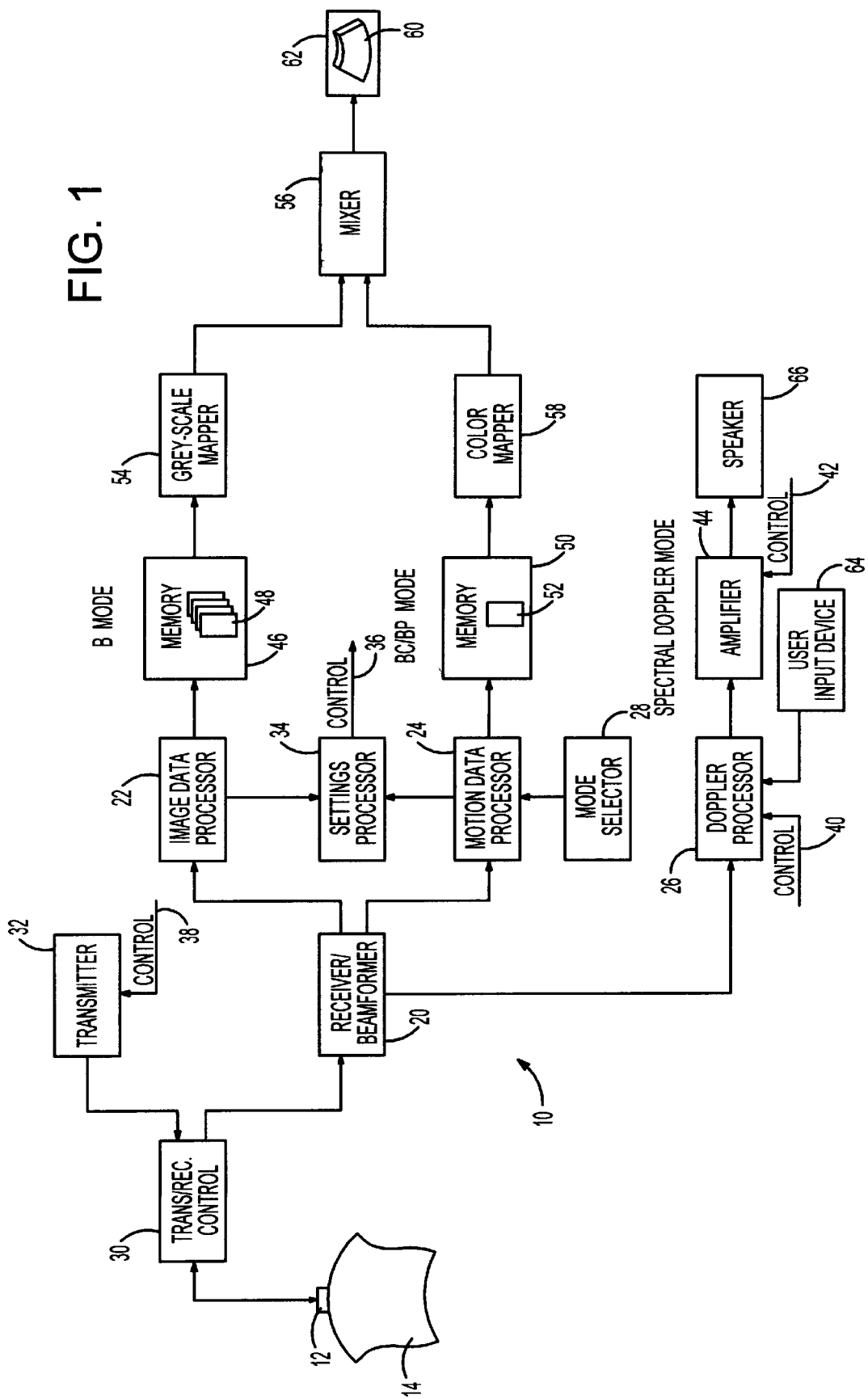
FIG. 1 is a block diagram of components of an ultrasonic system that is enabled to automatically determine settings for a spectral Doppler mode of operation in accordance with the invention.

With reference to FIG. 1, an ultrasonic imaging system 10 is shown as including a transducer 12 in contact with the skin of a patient 14. The structure of the transducer is not critical to the invention. In one embodiment, the transducer includes an array of 192 piezoelectric elements that are used to generate ultrasonic beams. An ultrasonic beam may be steered or focused using techniques well known in the art. By detecting the reflections from a region of interest (i.e., sample volume) within the patient 14, the region can be imaged.

The system 10 has a number of alternative modes of operation. The modes are partially represented as three separate paths from a receiver/beamformer 20. The first path is a B mode path that includes an image data processor 22. The second path is designated as the BC/BP mode path that begins with a motion data processor 24. The third path is identified as the spectral Doppler mode path and begins with a Doppler processor 26. A mode selector 28 allows the BC/BP mode path to be switched between a colorflow mode and a power mode. The colorflow mode provides ultrasound-based motion data that is direction dependent (i.e., velocity data), while the power mode provides ultrasound-based data that is direction independent (i.e., speed date). While the system 10 may be set to operate in any of four modes, this is not critical. Alternatively, the spectral Doppler mode may be coupled with only one of the other modes.

A transmitter/receiver control device 30 alternates between connecting the transducer 12 with a transmitter 32 and with the receiver/beamformer 20. The transmitter provides electrical signals to the transducer for generating ultrasonic beams. An acoustically conductive lubricating agent may be applied to the skin of the patient 14 to improve acoustic coupling between the transducer and the patient. The ultrasonic beams propagate into the patient and are reflected by anatomical features, such as blood vessels. Echoes return through the skin to the transducer and are converted to electrical signals that are sent to the receiver/beamformer 20 for amplification. The beam forming is typically a digital process, so that an analog-to-digital converter is required.

Image interrogation beams that are generated during operation of the system 10 in the B mode often have properties that are distinguishable from properties of motion interrogation beams generated during the operation of the system in either the colorflow or power mode. Conventionally, the image interrogation beams have a direction that is perpendicular to the transducer 12, since the acquisition of image data is dependent upon sensing echoes from tissue. The motion interrogation beams may be perpendicular to the transducer or may be directed at an acute angle to the transducer, since the motion data that is to be acquired is partially based on the angle between the beam and the anatomical feature that is in motion. As is well known in the art, when a motion interrogation beam is dispersed by flowing blood cells, the frequency of the beam is subjected to Doppler shift. Echo signals are processed at the motion data processor 24 to determine the velocity or speed of motion. There may be additional differences between the two types of beams, such as the difference in the duty cycles.

Similarly, there are differences between the operation of the system 10 in the spectral Doppler mode, as compared to any of the other three modes of operation. For example, the settings for operational parameters such as the pulse repetition frequency (PRF), angle correction, gain and sample volume placement may be specific to the spectral Doppler mode. Typically, the spectral Doppler mode follows imaging in at least one of the other three modes. In accordance with the invention, a settings processor 34 is enabled to determine initial settings for the spectral Doppler mode. The initial settings are based upon the image data or the motion data that is acquired before the spectral Doppler mode is initiated. The settings processor 34 generates control signals that are output via an output line 36. While not shown in FIG. 1, the output line 36 is connected to a control input 38 to the transmitter 32, a control input 40 to the Doppler processor 26, and a control input 42 to an amplifier 44. By determining the settings in parallel with the conventional signal manipulation that takes place when the system 10 is in the B mode and/or the BC or BP mode, the system is programmed to establish the initial settings in a manner consistent with the other determinations formed during a particular session. That is, the initial spectral Doppler settings are not based upon an "average" examination, but are at least partially based upon information acquired during the particular session in which the settings are to be implemented. Since the settings may vary significantly from session to session, this may reduce the examination time and improve the diagnostic results for spectral Doppler examinations.

In the B mode of operation, the image information is directed to the image data processor 22. Frames of two-dimensional image information are acquired by memory 46 and are stored as arrays of pixel values. In FIG. 1, four frames 48 of pixel values are represented. If a three-dimensional image is to be constructed from the frames, each frame represents a cross section along a different plane of the patient 14. The different cross sectional images are then combined to form the three-dimensional image.

The motion data processor 24 is connected to memory 50 for generating a frame 52 of motion data. The frame 52 may be a pixel array of color-coding values. The processor 24 may operate in a velocity-based mode or a power-based mode, depending upon the state of the mode selector 28. As is known in the art, for each pixel value in the frame 52, the motion data processor 24 performs algorithmic operations on an ensemble of echo signals. Samples from a given depth are taken at a pulse repetition frequency that is determined by the rate of transmissions of motion interrogation beams by the transducer 12. The process is described in greater detail in U.S. Pat. No. 5,443,071 to Banjanin et al., which is assigned to the assignee of the present invention.

Optionally, the system 10 can be operated simultaneously in the B mode and one of the BC and BP modes. The frame rates for acquiring the image frames 48 and the motion frames 52 are independently selected and the two types of frames are concurrently acquired. For example, during the time that memory 50 stores the motion data to generate the single motion frame 52, the four image frames 48 may be generated in the memory 46. A grey-scale mapper 54 and a mixer 56 cooperate with a color mapper 58 to form a composite image 60 at a display device 62. Superimposing the motion data on the grey-scale image is well known in the art.

When the system 10 is switched to the spectral Doppler mode, the Doppler processor 26 performs the operations conventionally associated with spectral Doppler processing. The initial settings for operation parameters are at least partially determined by calculations of the settings processor 34, as will be explained more fully below. A clinician can make modifications to the settings by operating a user input device 64, which may be a keyboard, dial controls, switches or the like.

The gain setting that is utilized at the initialization of the spectral Doppler mode is determined at the settings processor 34 as a function of the amplitude of signals received during the operations of the image data processor 22 and the motion data processor 24. The control output 36 of the settings processor is connected to the control input 42 to the amplifier 44. While the output of the Doppler mode processing is represented as being a speaker 66, this is not critical. Alternatively, a display of a velocity spectrum plotted against time may be substituted for or added to the speaker 66.

The settings processor 34 may also be used to determine the PRF setting. This setting is communicated to the transmitter 32 via the control input 38. An angle correct setting may be communicated to the Doppler processor 26 via a control input 40. While not shown, the sample volume placement for the spectral Doppler mode may also be automatically determined and may be communicated to the appropriate circuitry by operation of the settings processor 34.

In the preferred embodiment, the processing to acquire two-dimensional images is performed in real-time and the settings processor 34 is operated to simultaneously calculate the initial settings for switching the system 10 into the spectral Doppler mode. This parallel processing is possible without significantly affecting the hardware on a conventional processing board of an ultrasonic system. In fact, it is likely that the processing can be enabled merely by adding additional software to commercially available systems.

DETERMINING D MODE SETTINGS FROM BC MODE INFORMATION

Figure 2:
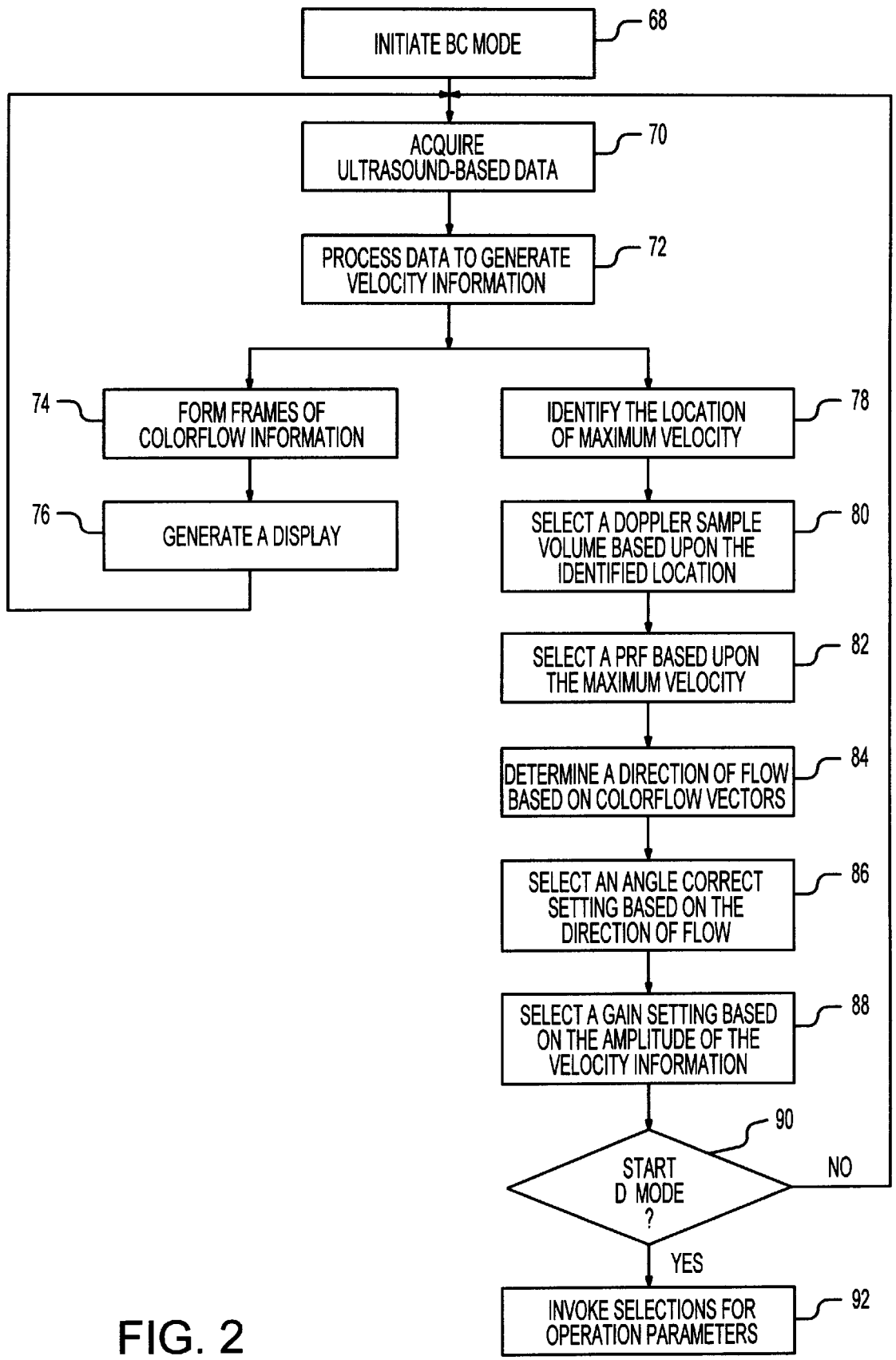
FIG. 2 is a process flow of steps to determine the initial settings for the spectral Doppler mode when the system of FIG. 1 is switched from a colorflow mode.

In the embodiment of FIG. 2, settings for operation parameters of a spectral Doppler mode are based upon information acquired in an ongoing colorflow imaging procedure. In step 68, the BC mode is initiated. A number of steps are executed using well known techniques. Firstly, the transducer 12 of FIG. 1 is used to acquire the conventional ultrasound-based data at step 70. The data is processed at step 72 to generate velocity information. Referring to FIG. 1, the processing takes place at the motion data processor 24. In step 74, frames 52 of colorflow information are stored at the memory 50. Using the color mapper 58, the step 76 of generating a display at the unit 62 is completed. The operations that occur in executing steps 68–76 are not critical to the invention.

Selections for settings of operation parameters for a subsequent D mode operation are determined in parallel with the steps 74 and 76 of generating a display of the colorflow information. The settings are determined using the settings processor 34 of FIG. 1. At step 78, the location of maximum velocity is identified. The maximum velocity detected in the colorflow image is a likely target of interest when the ultrasonic system 10 is switched to D mode operation. Consequently, in step 80, a spectral Doppler sample volume is selected based upon the identified location of maximum velocity. The spectral Doppler sample volume could initially be centered upon the location of the maximum velocity in order to provide a more accurate and repeatable sample volume determination, as compared to the conventional method of requiring a clinician to visually select the location. In order to improve the robustness of the estimate at steps 78 and 80, the maximum velocity could be calculated over several images and several pixels.

In step 82, the PRF is selected for implementation when the ultrasonic system 10 is switched to the D mode. The maximum velocity detected in the colorflow image can be used to calculate the spectral Doppler mode PRF setting. The Doppler PRF should be set so that the frequency range above and below the baseline (depending on the type of examination that is in session) is greater than the maximum frequency shift detected in the colorflow data. A margin of a few percent may also be incorporated into the determination of the setting in order to avoid aliasing.

In step 84, the direction of flow is determined on the basis of colorflow vectors. This can be accomplished in a number of alternative methods. For example, a line could be fit between the locations of maximum velocities in multiple colorflow vectors around the sample volume location of the BC mode. Alternatively, a line could be fit between the locations of the peak cross-correlation coefficients calculated on the colorflow vectors around the sample volume location. These calculations would provide a basis for selection of an angle correct setting at step 86. A less desirable manner of determining the angle correct setting would be to base the angle correct to be parallel to the boundaries of the colorflow signal in the vectors around the location of the sample volume. This would not be directly related to the actual flow direction, but would allow the initial setting to be based upon the information from the ongoing session, rather than the "average" session.

A gain setting is selected in step 88. The gain setting is based upon the amplitude of the colorflow data around the sample volume. It is likely that the D mode signal strength will be proportional to the colorflow signal strength, so this basis for the gain setting is reasonably reliable.

After selections for the spectral Doppler sample volume, the Doppler PRF, the angle correct, and the gain have been determined in steps 78–88, the decision step 90 is implemented. If the D mode is to be initiated, the selections for the operation parameters are invoked at step 92. Referring to FIG. 1, the settings are calculated at the settings processor 34 and are output via the control line 36 to the input control lines 38, 40 and 42. Other control lines may be added as needed. Returning to step 90, if the D mode is not to be initiated, the process returns to step 70 of acquiring ultrasound-based data for updating the selection of the settings in steps 78–88, as well for generating a display at step 76.

By initiating the D mode based upon information acquired from the ongoing session, the D mode is likely to be started in a condition that requires less manipulation by the clinician than when the prior art methods of basing settings on the "average" session are used. Any manipulation that is required may be provided using the user input device 64.

DETERMINING D MODE SETTINGS FROM BP MODE INFORMATION

If the ultrasonic system 10 of FIG. 1 is in the BP mode prior to the switch to the spectral Doppler mode, a reduced amount of information is available as the basis for selecting parameter settings for the spectral Doppler mode. However, many of the parameter settings can still be estimated.

Figure 3:
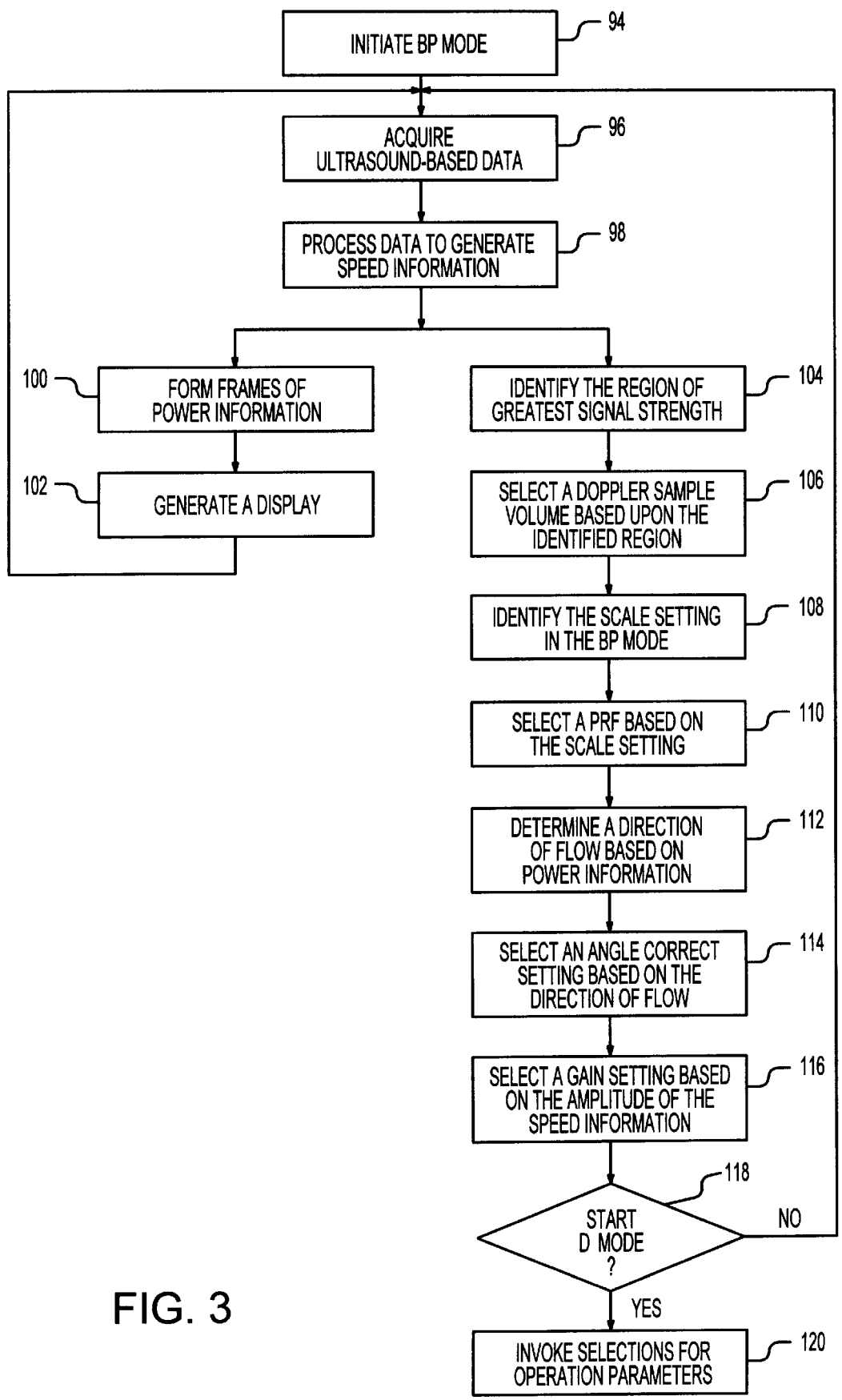
FIG. 3 is a process flow of steps for determining the initial settings for the spectral Doppler mode when the system of FIG. 1 is switched from a power mode.

Referring to FIG. 3, the steps 94, 96 and 98 are conventional steps of initiating the BP mode, acquiring ultrasound-based data, and processing the data to generate speed information. In step 100, the speed information is used to form frames of power information, which enable a display to be generated at step 102. The steps 100 and 102 may be implemented using conventional techniques for forming a BP image.

In parallel with the steps 100 and 102 of forming the frames and generating the display, the settings processor 34 selects process parameters that are to be invoked when the system 10 is switched to D mode operation. At step 104, the region having the greatest signal strengths is identified. The strongest signals are typically produced in the region with the highest flow velocity. The region of the power mode image with the highest amplitude can reasonably be used to select the spectral Doppler sample volume, as indicated at step 106. While the basis for selecting the spectral Doppler sample volume is less than ideal, it is an improvement over the conventional techniques. At the very least, power mode data provides a highly reliable basis for locating the initial Doppler sample volume inside a blood vessel.

The maximum velocity information is not available from BP imaging, but the scale setting for the power mode acquisition of ultrasound-based data can be used as a start point. That is, if the scale setting for the display of a BP image is used in place of the calculated maximum frequency shift, the Doppler PRF can be determined in the same manner as described with reference to step 82 in FIG. 2. Thus, the Doppler PRF should be set so that the frequency range above and below the baseline is greater than the maximum frequency shift, as indicated by the scale setting. In FIG. 3, the scale setting is determined in step 108 and the PRF is selected in step 110.

In step 112, the direction of flow is determined. The method of detecting the flow direction may be similar to the techniques described with reference to step 84 in FIG. 2, except power mode data would be used in the place of colorflow data. In step 114, an angle correct setting is selected based upon detection of the flow direction.

Another setting for an operation parameter is selected at step 116. The amplitude of the power mode data is directly related to the amplitude of signals that will be acquired when the ultrasonic system 10 is switched to the spectral Doppler mode. Consequently, a D mode gain setting can be selected on the basis of the amplitude of the speed information acquired and processed in steps 96 and 98.

Decision step 118 determines whether the ultrasonic system 10 is to be switched to the D mode. If an affirmative response is received at decision step 118, the selections that were made in steps 104–116 are invoked at step 120, thereby providing initial settings for operation parameters within the D mode. On the other hand, if a negative response is generated at the decision step 118, the process returns to step 96 in order to allow subsequently acquired ultrasound-based data to update the selections of process parameters. The most recent selections of process parameters are invoked at step 120 when an affirmative response is generated at step 118.

DETERMINING D MODE SETTINGS FROM B MODE INFORMATION

Figure 4:
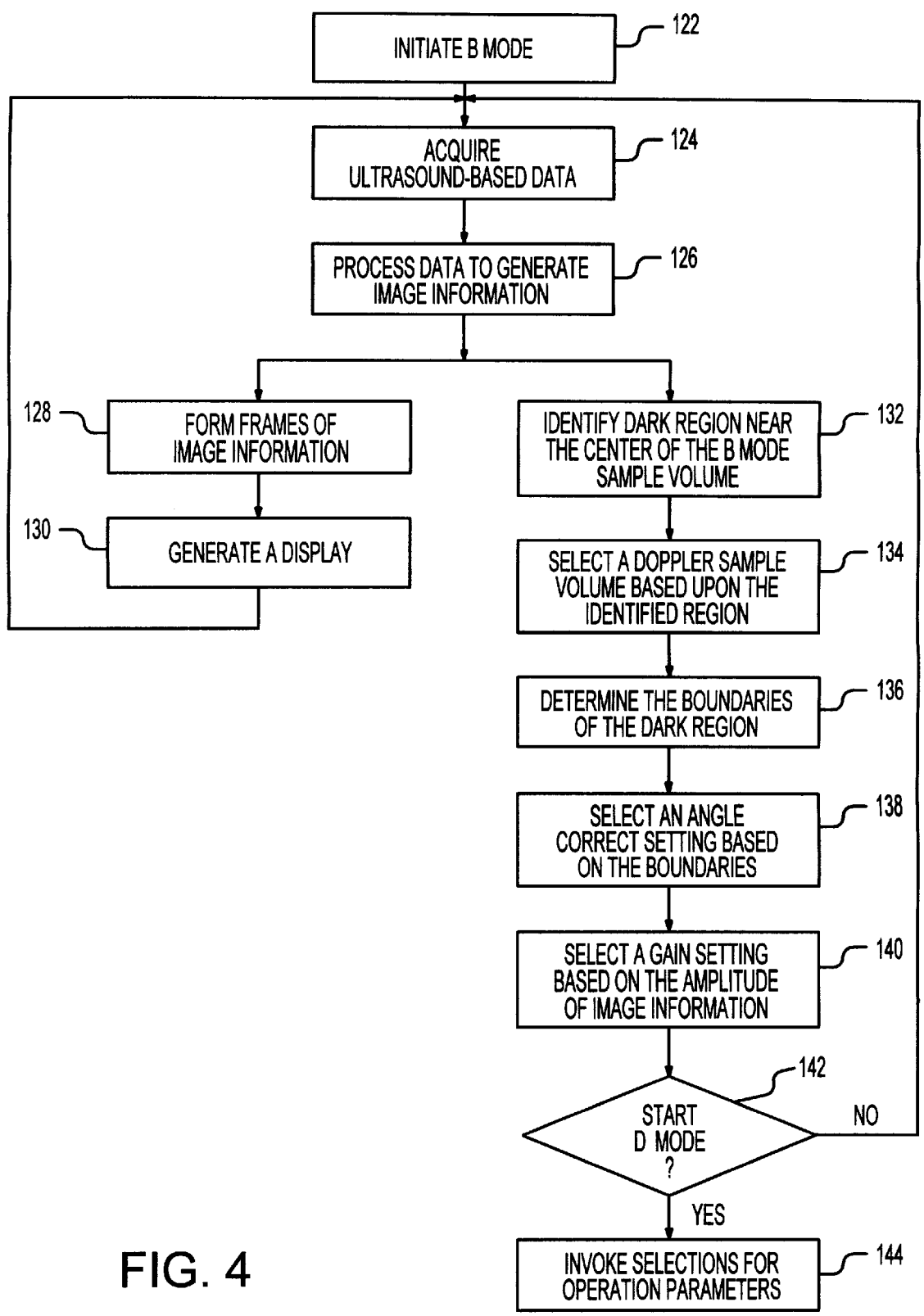
FIG. 4 is a process flow of steps for determining the initial settings for the spectral Doppler mode when the system of FIG. 1 is switched from the B mode.

The process flow of FIG. 4 is utilized when the ultrasonic system 10 of FIG. 1 is switched into the spectral Doppler mode from B mode operation. Typically, B mode imaging is executed simultaneously with colorflow or power imaging. Since the colorflow and power mode operations provide more information than is generated by B mode imaging, the process of FIG. 4 is followed only when the system is limited to B mode imaging.

Steps 122, 124 and 126 are conventional steps of initiating the B mode operation, acquiring ultrasound-based data, and processing the acquired data to generate image information. In FIG. 1, the transducer generates ultrasonic beams and forms electrical signals that are responsive to echoes of the beam energy from the patient 14. This acquired ultrasound-based data is processed at the image data processor 22. In step 128, the memory 46 stores frames 48 of the image information. The grey-scale mapper 54 is utilized to generate images at the display unit 62. In FIG. 4, the display is generated at step 130. The display may be a two-dimensional slice or a number of slices can be combined to form a three-dimensional image.

The settings processor 34 of the ultrasonic system 10 receives the image information from the processor 22 in order to select settings. At step 132, a dark region is identified near the center of the B mode sample volume. It is likely that the target for the subsequent spectral Doppler mode operation will be near the center of the image. For example, a blood vessel of interest will most likely be located near the center of the image. Consequently, in step 134, a Doppler sample volume is selected based upon the identified region. Once the dark region has been located, a search can be performed to determine the orientation of the boundaries of the dark region, as indicated at step 136. An angle correct setting can be selected in step 138 based upon the boundaries. The angle correct can be set to be parallel to the identified boundaries of the dark region.

At step 140, a gain setting is selected for the spectral Doppler mode of operation. The amplitude of the image information can be directly mapped to the selection of the beam setting, as described with reference to FIGS. 2 and 3.

In the decision step 142, a determination is made as to whether the ultrasonic system is to be switched to the D mode of operation. When a negative response is generated at this step, the process returns to the step 124 of acquiring ultrasound-based data. By providing a loop back to the acquisition of the ultrasound-based data, the settings selections can be continuously updated. When an affirmative response is finally generated at the decision step 142, the most recent selections are invoked at step 144. Fine tuning of the settings may be necessary, but the selections will be based upon information acquired during the ongoing session, rather than being based upon the "average" session.

While the process for selecting the D mode settings has been described as one in which the selection process occurs in parallel with the two-dimensional imaging, this is not critical. As an alternative, the settings selections may be triggered only by an indication that the ultrasonic system 10 is to be switched from a two-dimensional mode to the spectral Doppler mode. In this less preferred embodiment, the initiation of operation in the spectral Doppler mode is preceded by a momentary delay in which the processing for selecting settings is initiated and completed.

What is claimed is:

1. A method of initializing a spectral Doppler mode of operation for an ultrasonic system comprising steps of:
   acquiring ultrasound-based data during a two-dimensional mode of operation of said ultrasonic system, said ultrasound-based data being unique to a particular session;
   processing said ultrasound-based data using automated techniques to determine settings for operation parameters, where said operation parameters are specific to said spectral Doppler mode of operation and said settings are specific to said particular session; and
   automatically establishing said settings for said operation parameters for said spectral Doppler mode based upon said processing of said ultrasound-based data during said two-dimensional mode of operation.

2. The method of claim 1 wherein said step of acquiring said ultrasound-based data includes identifying a location of maximum velocity in a target volume when said ultrasonic system is in said two-dimensional mode of operation, said identified location being used in said processing step of determining said settings for said operation parameters.

3. The method of claim 2 wherein said step of processing said ultrasound-based data includes utilizing said identified location of maximum velocity to determine a spectral Doppler sample volume for said spectral Doppler mode of operation.

4. The method of claim 3 wherein said step of automatically establishing said settings includes centering said spectral Doppler sample volume based on said identified location of maximum velocity.

5. The method of claim 1 wherein:
said step of acquiring said ultrasound-based data includes determining velocities of movement within a sample volume of said two-dimensional mode of operation;
said step of processing said ultrasound-based data includes calculating a maximum frequency shift of echo signals used to determine said velocities and includes selecting a pulse repetition frequency (PRF) setting for said spectral Doppler mode of operation, said selection of a PRF setting being at least partially based on said calculated maximum frequency shift; and
said step of automatically establishing said settings includes establishing said selected PRF setting.

6. The method of claim 5 wherein said step that includes selecting said PRF setting includes determining a frequency range above and below a baseline such that said frequency range is greater than said maximum frequency shift of echo signals, said frequency range being a basis for said selection of said PRF setting.

7. The method of claim 1 wherein:
said step of processing said ultrasound-based data includes determining a direction of flow from image data acquired while said ultrasonic equipment is in said two-dimensional mode of operation, said step further including selecting an angle correct setting for application for spectral Doppler beam processing during said spectral Doppler mode of operation.

8. The method of claim 7 wherein said step that includes determining said direction of flow utilizes multiple colorflow vectors that are formed as said image data in said step of acquiring ultrasound-based data, said utilization of multiple colorflow vectors to determine said direction of flow including one of:
identifying a fit among locations of maximum velocity values of said multiple colorflow vectors; and
identifying a fit among locations of peak cross-correlation coefficients calculated for said colorflow vectors.

9. The method of claim 7 wherein said step that includes determining said direction of flow includes utilizing power mode data as said image data.

10. The method of claim 1 wherein:
said step of acquiring said ultrasound-based data is executed when said ultrasonic system is in a power mode; and
said processing step includes selecting a spectral Doppler sample volume based on identifying relatively high amplitude signals received during said power mode.

11. The method of claim 1 wherein said processing step includes utilizing amplitudes of said ultrasound-based data to determine a gain setting as one of said operation parameters for said spectral Doppler mode of operation.

12. A method of determining settings for a spectral Doppler mode (D-mode) of operation comprising steps of:
performing ultrasonic imaging during a first mode of operation different from said D-mode of a sample volume prior to initiating said D-mode of operation, including determining information by processing echo data obtained during said ultrasonic imaging; and
identifying settings for operation parameters that are potentially different for said D-mode of operation than for said step of performing ultrasonic imaging, including basing said settings on manipulating said information determined by processing said echo data, said operation parameters including a plurality of spectral Doppler sample placement, an angle correct setting, gain, and a pulse repetition frequency (PRF) setting.

13. The method of claim 12 further comprising a step of automatically establishing said settings at a start of said D-mode of operation.

14. The method of claim 13 wherein said step of identifying said settings includes utilizing flow data as a basis for computing said settings, said flow data being acquired in one of a power mode or a color mode of said ultrasonic imaging.

15. An ultrasonic system comprising:
transducer means for transmitting and receiving ultrasonic energy to and from a body of interest;
first processing means in communication with said transducer means for forming image data of said body of interest based on ultrasonic energy received at said transducer means, said first processing means having a two-dimensional mode of operation and a spectral Doppler mode of operation;
second processing means in communication with said first processing means for determining settings for operation parameters that are specific to said spectral Doppler mode of operation, said second processing means being configured to manipulate said image data formed when said first processing means is in said two-dimensional mode such that said settings are specific to an ultrasound session in which said settings are determined.

16. The ultrasonic system of claim 15 further comprising a means responsive to said second processing means for automatically adjusting at least one of said transducer means and said first processing means to implement said settings when said first processing means is switched from said two-dimensional mode to said Doppler mode of operation.

17. The ultrasonic system of claim 15 wherein said second processing means is configured to manipulate velocity data to identify a location of maximum velocity when said first processing means is in said two-dimensional mode and to select a setting for a spectral Doppler sample volume based upon identifying said location.

18. The ultrasonic system of claim 15 wherein said second processing means is configured to calculate a maximum velocity shift exhibited by velocity data when said first processing means is in said two-dimensional mode and to select a PRF setting for said spectral Doppler mode based upon said maximum velocity shift.

19. The ultrasonic system of claim 15 wherein said second processing means is configured to determine a direction of flow when said first processing means is in said two-dimensional mode and to select an angle correct setting for application during said spectral Doppler mode.

* * * * *